US008419669B2

(12) United States Patent
Bejarano (10) Patent No.: US 8,419,669 B2
(45) Date of Patent: Apr. 16, 2013

(54) BRACE HINGE WITH TELESCOPING CONDYLE PAD

(75) Inventor: Robert Bejarano, San Marcos, CA (US)

(73) Assignee: DJO, LLC, Vista, CA (US)

( * ) Notice: Subject to any disclaimer, the term of this patent is extended or adjusted under 35 U.S.C. 154(b) by 432 days.

(21) Appl. No.: 12/378,121

(22) Filed: Feb. 10, 2009

(65) Prior Publication Data

US 2010/0010409 A1    Jan. 14, 2010

Related U.S. Application Data

(60) Provisional application No. 61/079,057, filed on Jul. 8, 2008.

(51) Int. Cl.
*A61F 5/00* (2006.01)
*E05D 11/10* (2006.01)
*E05D 15/22* (2006.01)

(52) U.S. Cl.
USPC .................................. 602/16; 16/333; 49/188

(58) Field of Classification Search ................. 602/4, 5, 602/1, 16, 21, 22, 23, 24, 25, 26, 27; 16/334, 16/368, 369; 49/188, 388, 397
See application file for complete search history.

(56) References Cited

U.S. PATENT DOCUMENTS

| 4,697,583 | A | * | 10/1987 | Mason et al. | 602/26 |
| 6,413,232 | B1 | | 7/2002 | Townsend et al. | |
| 2006/0287624 | A1 | * | 12/2006 | Popp et al. | 602/16 |
| 2007/0244419 | A1 | * | 10/2007 | Mason et al. | 602/16 |
| 2008/0097269 | A1 | * | 4/2008 | Weinberg et al. | 602/16 |
| 2008/0177208 | A1 | * | 7/2008 | Borschneck | 602/16 |

FOREIGN PATENT DOCUMENTS

| GB | 2 327 044 | 1/1999 |
| WO | WO-2005/107659 | 11/2005 |
| WO | WO-2007/120516 | 10/2007 |

* cited by examiner

*Primary Examiner* — Patricia Bianco
*Assistant Examiner* — Tarla Patel
(74) *Attorney, Agent, or Firm* — Ropes & Gray LLP (57) ABSTRACT

A knee brace assembly is provided having an adjustable, pressure-applying gear system mounted to a portion of the hinge assembly. Through selective adjustment of the gear system, the knee brace assembly can apply pressure to a portion or portions of the knee joint, thereby relieving pressure on the knee joint. A method of treating a knee joint using a knee brace assembly including a planetary gear system is also provided.

20 Claims, 8 Drawing Sheets

BRACE HINGE WITH TELESCOPING CONDYLE PAD

RELATED APPLICATIONS

This application claims the priority benefit under 35 U.S.C. §119(e) to U.S. Provisional Patent Application Ser. No. 61/079,057 filed Jul. 8, 2008, the entirety of which is hereby expressly incorporated by reference herein.

FIELD

The present application relates to orthopedic braces. More particularly, the present application describes an adjustment system for a brace.

BACKGROUND

Orthopedic knee braces are typically worn either to support a healthy knee joint and prevent injury, or to stabilize a knee joint that has been destabilized by an injury or other condition. These braces generally include rigid structural components that support or stabilize the knee joint. The rigid structural components are dynamically linked together by one or more hinges that enable controlled pivotal movement of the knee joint during user activity or rehabilitative therapy. The brace is positioned on the leg such that the hinges traverse the knee joint, while the rigid components are secured to the leg above and below the knee joint.

Osteoarthritis is a degenerative disease that destabilizes the knee joint. The disease commonly results from aging, knee joint overuse, or injury. A person afflicted with osteoarthritis suffers chronic pain when his or her knee joint is statically or dynamically loaded. The pain is caused by an unbalanced loading on the knee joint. The unbalanced loading closes a compartment between the condyles of the femur and tibia, and when these condyles contact one another, their contacting surfaces develop painful abrasions.

Wearing an orthopedic knee brace on the affected leg is one common noninvasive method of treating osteoarthritis pain. These braces apply a force to a medial or lateral side of the knee in order to unload the affected compartment of the knee joint and eliminate contact between the femur and tibia. U.S. Pat. No. 5,277,698 discloses an example of such a brace. This brace applies a force to the knee on that side of the knee remote from the compartment having osteoarthritis as the knee moves to extension. Preferably, the force is applied at a point about 10° to 15° posterior of the normal axis of rotation of the knee.

U.S. Pat. No. 5,586,970 discloses a knee brace having a medial condyle pad and a lateral condyle pad that are each independently adjustable in side-to-side motion. This independent adjustment permits either medial condyle pad or lateral condyle pad to have variable pressure with respect to a user's knee.

U.S. Pat. No. 5,807,294 discloses a hinge assembly for an orthopedic knee brace that pivotally couples an upper arm and a lower arm. The hinge assembly includes a pad assembly a hinge and upper and lower adjustment members enabling adjustment of the normal force applied by the hinge assembly to the knee joint for the treatment of osteoarthritis. The hinge includes an end of the upper arm, an end of the lower arm, outer and inner hinge plates positioned on opposite sides of the ends, and upper and lower hinge fasteners. The upper and lower hinge fasteners each have a bore therethrough that is internally threaded. The upper hinge fastener rotatably connects the end of the upper arm to the outer and inner hinge plates, and the lower hinge fastener rotatably connects the end of the lower arm to the outer and inner hinge plates. The upper adjustment member has external threads that are received by the internal threads of the upper hinge fastener to telescopically couple the upper adjustment member to the upper hinge fastener. The lower adjustment member likewise has external threads that are received by the internal threads of the lower hinge fastener to telescopically couple the lower adjustment member to the lower hinge fastener. Both the upper and lower adjustment members have ends that are substantially fixedly coupled to the pad holder. As a result, the pad assembly is selectively displaceable toward or away from the hinge when the user selectively displaces the upper and lower adjustment members through the upper and lower bores of the upper and lower hinge fasteners.

However, the braces of the foregoing are difficult to use and not as precisely adjustable as may be desired. For example, the adjustment members often include screws, bolts, and/or other fasteners which are adjusted individually, often requiring the use of tools or more than one hand. Accordingly, improvements in bracing loading mechanisms are needed.

SUMMARY OF THE INVENTIONS

An aspect of at least one of the embodiments disclosed herein includes the realization that knee brace assemblies can have multiple components and/or adjustment members for selectively displacing a condyle pad towards or away from a knee joint. A pad adjustment system according to the disclosed systems provides a single component which is turned or moved by one hand to cause desired displacement of the condyle pad.

Another aspect of at least one of the embodiments disclosed herein includes the realization that knee braces which displace a condyle pad towards or away from a knee joint during each pivoted rotation of the hinge assembly can cause component wear and tear in the pad adjustment system. A pad adjustment system which is independent from the hinge assembly, and remains fixed during hinge assembly rotation, is likely to last longer and require less maintenance.

Thus, in accordance with an embodiment, a knee brace assembly can comprises a hinge assembly, a proximal arm pivotably engaging the hinge assembly, a distal arm pivotably engaging the hinge assembly, and a pad adjustment system.

In one representative embodiment, a knee brace assembly is provided with a hinge assembly. The knee brace also includes a proximal arm and a distal arm both pivotably engaging the hinge assembly. The knee brace includes a pad adjustment system having a first gear member operatively connected to a portion of the hinge assembly and a second gear member engaged with the first gear member and configured to rotate within the pad adjustment system. The pad adjustment system also includes a third gear member engaged with the second gear member and being actuatable by a user. The knee brace also includes a driven member operatively connected to the second gear member, where the driven member is configured to extend away from the hinge assembly upon actuation of the third gear member. In certain embodiments, the third gear member is rotatably actuatable by a patient or physician.

According to one implementation, the knee brace assembly includes a sun gear that is operatively connected to a portion of the hinge assembly. The knee brace assembly also includes at least one planetary gear engaged with the sun gear, where the planetary gear includes a set of gear teeth and threaded grooves. The knee brace assembly also includes a ring gear engaged with at least one planetary gear. The knee brace assembly also includes at least one threaded fastener partially received within the threaded grooves of at least one planetary gear. The knee brace assembly also includes a telescoping plate connected to at least one fastener. In certain embodiments, the knee brace assembly includes a pad adjustment system having a plurality of planetary gears configured to engage with and revolve around the sun gear. In certain embodiments, the knee brace assembly includes a base member configured to connect to the hinge assembly and a sun gear tray integrally formed with the sun gear. The sun gear tray is configured to connect to the base member. In certain embodiments, the knee brace assembly also includes a ratchet mechanism between the sun gear tray and the ring gear. According to one implementation, at least one planetary gear is configured to both revolve about the sun gear and rotate about at least one planetary gear's own axis. In certain embodiments, the knee brace assembly also includes threaded grooves that are located on a fastener insert positioned in at least one planetary gear.

According to one implementation, the knee brace assembly includes a ring gear having a set of gear teeth on an inner annular surface configured to contact at least one planetary gear. In certain embodiments, the ring gear includes at least one gripping surface along a radially outer surface. At least one gripping surface includes a cup-shaped section of material on the ring gear.

According to one implementation, the knee brace assembly includes a locking member engaged with the third gear member by a locking ledge. In certain embodiments, the locking ledge includes a plurality of ratcheting protrusions configured to engage grooves on the third gear member. According to one implementation, the knee brace assembly includes ratcheting protrusions that resist rotation between the third gear member and first gear member in at least one direction.

According to one implementation, the knee brace assembly includes at least one threaded fastener that is configured to attach to the telescoping plate in a manner which prevents rotation of at least one threaded fastener. In certain embodiments, the knee brace assembly includes a pad that is coupled to the driven member. The knee brace assembly also includes a cover plate for a gear member. The knee brace assembly also includes a cover stop configured to prevent the gear member from translating axially.

According to one implementation, a knee brace assembly configured to off-load a patient's knee is provided. The knee brace assembly includes a gear system coupled to an inner side of a hinge assembly of the knee brace. The gear system includes a first gear, a plurality of second gears engaged with the first gear, a third gear in rotating engagement with the second gears, and a telescoping plate engaged with a second gear by a coupling. The rotation of the third gear causes the telescoping plate to be displaced along the coupling.

According to one implementation, a method for adjusting the amount of pressure applied to a knee joint is provided. The method includes securing to an inner side of a hinge assembly of a knee brace a gear system and turning, by hand, a knob of the gear system to simultaneously cause a plurality of revolving gear members to drive a telescoping plate towards or away from the knee joint. The method also involves adjusting the position of the telescoping late until a desired level of pressure against the knee joint is achieved. Other features and embodiments are disclosed herein.

BRIEF DESCRIPTION OF THE DRAWINGS

These and other features and advantages of the present embodiments will become more apparent upon reading the following detailed description and with reference to the accompanying drawings of the embodiments, in which.

DETAILED DESCRIPTION OF THE PREFERRED EMBODIMENTS

An embodiment of an improved brace assembly 10 is disclosed herein and illustrated with reference to FIGS. 1-5. The embodiments disclosed herein are described in the context of a knee brace because the embodiments disclosed herein have particular utility in this context. However, the embodiments and inventions herein can also be applied to types of braces configured for other environments, including but not limited to shoulders, backs, elbows, and hips.

Figure 1:
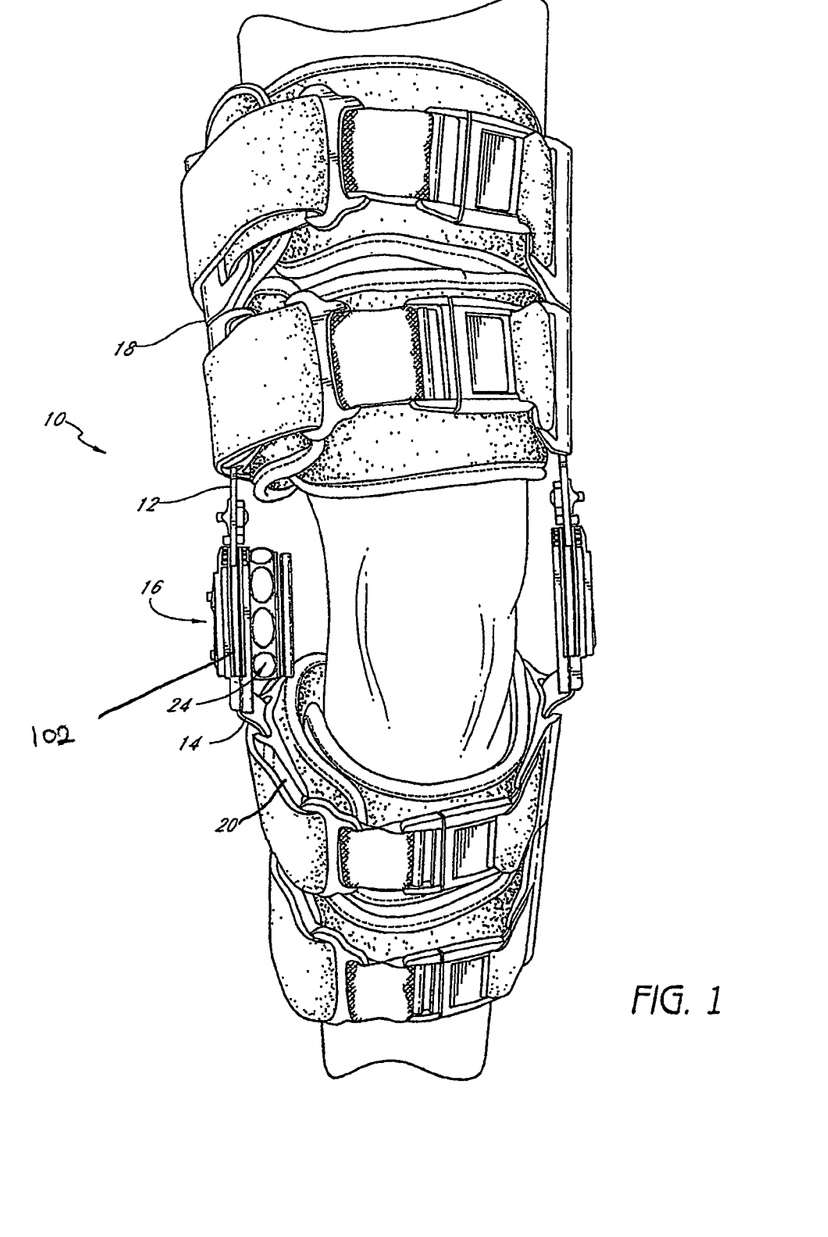
FIG. 1 is a front side elevational view of an embodiment of a knee brace assembly on a leg, including a pad adjustment system.

With reference to FIG. 1, the brace assembly 10 can be adapted for use on a lateral side of a right leg, or a medial side of a left leg. Those of skill in the art will appreciate that a substantially identical hinge having a mirror image configuration can be adapted for use on a medial side of a right leg, or a lateral side of a left leg. For simplicity, the present brace assembly 10 is described with reference to a lateral side of a right leg. The scope of the present brace assembly 10 is not, however, limited to an application of a lateral side of a right leg.

The brace assembly 10 includes, among other features, a proximal arm 12 and a distal arm 14 pivotably engaging a hinge assembly 16. As shown, the hinge assembly 16 comprises a lateral hinge plate and a medial hinge plate. The proximal arm 12 is substantially flat plate having a hinge-engaging portion at a distal end, and an upright-engaging portion at a proximal end. The upright-engaging portion is substantially rectangular, while the hinge-engaging portion has a complex perimeter, including an anterior shoulder, a posterior shoulder, and a plurality of gear teeth (not shown) along proximal and posterior edges. The proximal arm 12 also includes a pivot aperture (not shown) near the distal end.

The distal arm 14 has gear teeth configured for contact with the gear teeth of proximal arm 12 and a pivot aperture (not shown) located near its proximal end.

With continued reference to FIG. 1, the proximal arm 12 engages a rigid proximal upright 18, and the distal arm 14 engages a rigid distal upright 20. The proximal and distal uprights 18, 20 are secured to the wearer's thigh and calf, respectively, with straps, cuffs, or other suitable attachment devices. The uprights and their attachment devices anchor the brace assembly 10 to the wearer's leg and enable the brace to provide the advantages outlined below.

The proximal and distal arms 12, 14 are sandwiched between the lateral and medial hinge plates such that the pivot apertures on the proximal and distal arms 12, 14 are coaxial with corresponding apertures on the hinge plates. The proximal and distal arms 12, 14 may be attached to the hinge plates with rivets or other suitable attachment members that allow the proximal and distal arms to pivot with respect to the hinge plates. Those of skill in the art will appreciate that other attachment devices and methods can be used in place of the attachment configuration described above.

Additionally, in at least one embodiment, an extension stop is optimally mounted to a lateral face of the medial hinge plate. The anterior and/or posterior shoulders of each arm 12, 14 cooperate with the extension stop to define a maximum extension angle for each arm 12, 14.

With continued reference to FIG. 1, an axis of rotation of the proximal arm 12 is parallel to, but spaced from, an axis of rotation of the distal arm 14. Such a bicentric hinge assembly more closely approximates the bending dynamics of the human knee, as is well understood in the art of orthopedic bracing. Those of skill in the art will appreciate, however, that the features and advantages of the present brace assembly 10 can also be achieved with a monocentric hinge.

With reference to FIGS. 1-4, the brace assembly 10 also includes a pad adjustment system 24. The pad adjustment system 24 can be used to adjust a condyle pad towards or away from a knee joint through use of a gear system. The pad adjustment system 24 is independently attached to the hinge assembly 16 and operates independently from the hinge assembly 16. In at least one embodiment, the pad adjustment system 24 incorporates a telescoping portion or portions which move a condyle pad to a desired position based on user input.

Figure 2:
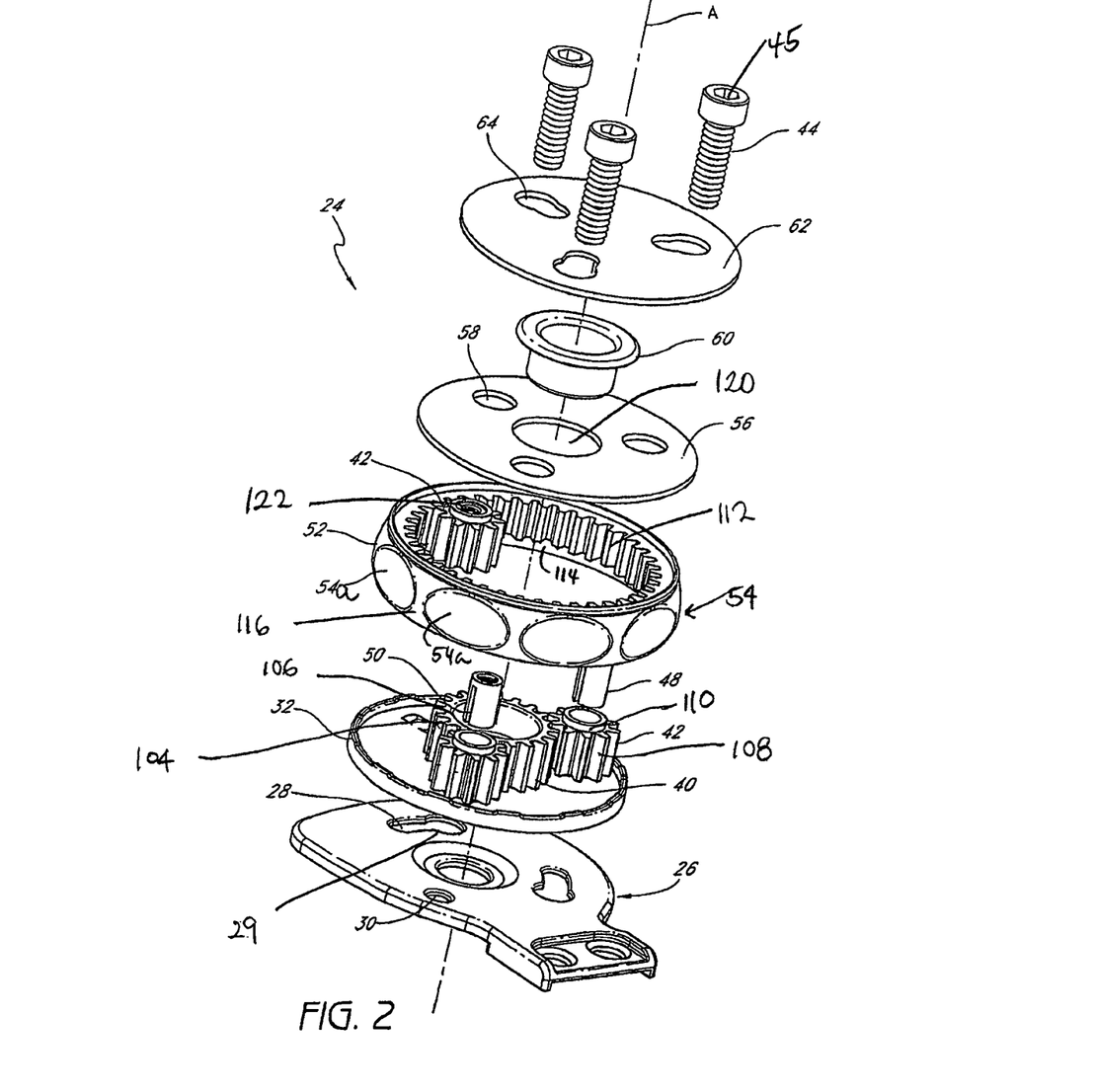
FIG. 2 is a top, front, and left side exploded view of an embodiment of an exemplary pad adjustment system.
Figure 3:
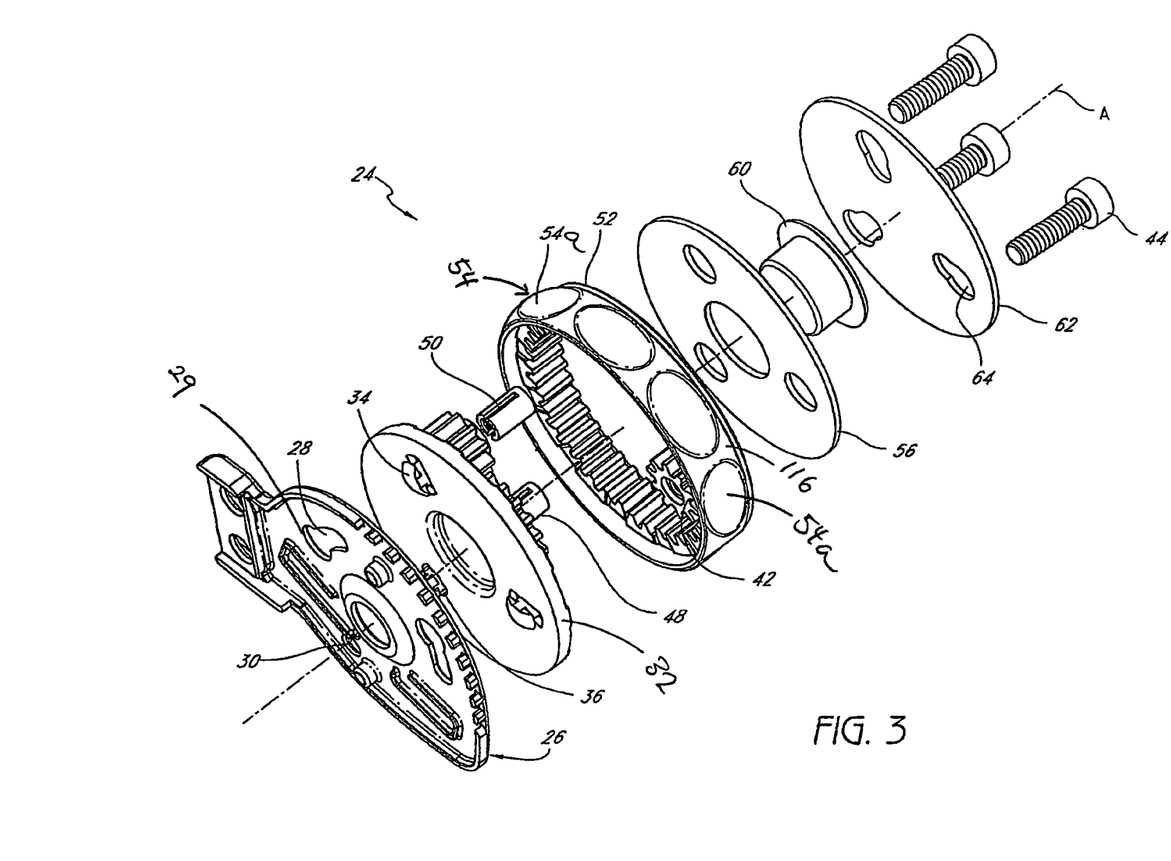
FIG. 3 is a bottom, back, and right side exploded view of the pad adjustment system of FIG. 2.
Figure 4:
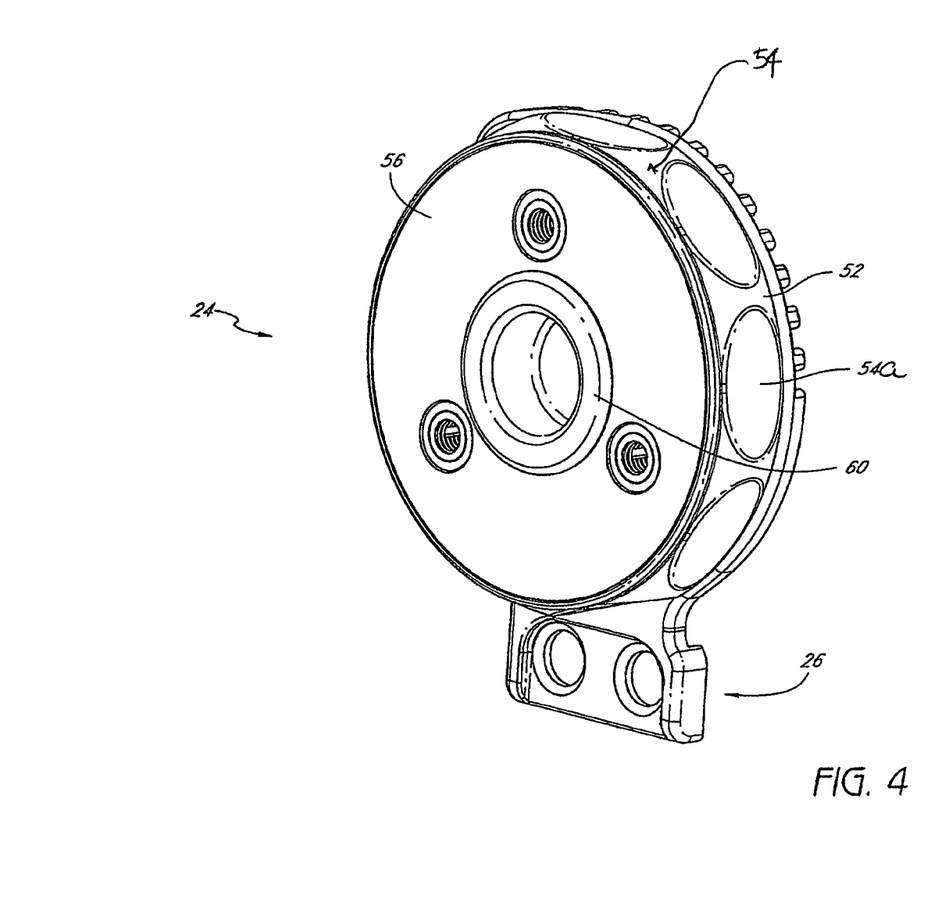
FIG. 4 is a top, back, and right side perspective view of the pad adjustment system of FIG. 2, without the telescoping plate and fasteners.

With reference to FIGS. 2-4, the pad adjustment system 24 includes, among other features, a fixed gear member, at least one rotating gear member, and an actuating gear member. The rotating gear member rotates about the center axis of the fixed gear member in response to a user rotating the actuating gear member. In certain embodiments, the fixed gear member and the rotating gear member each include teeth sized and shaped to permit and facilitate such rotation. The rotation causes a driven member to extend laterally from the pad adjusting system to off-load the knee. As shown, an exemplary fixed gear member is a sun gear 40, and an exemplary rotating gear member is a planetary gear 42 having three revolving gear members that revolve around the sun gear 40. An exemplary actuating gear member is a ring gear 52.

FIGS. 2 and 3 show an exploded view of a exemplary pad adjustment system 24. As shown, the pad adjustment system 24 includes a sun gear tray 32, which houses the sun gear 40, having at least one mating portion 34 that protrudes from the bottom surface of the sun gear tray 32. The mating portion 34 is used to connect the sun gear tray 32 to a base member 26. The mating portion 34 is sized and shaped to be positioned within a slot 28 of the base member 26. As shown in FIG. 3, the slot 28 has a larger radius 29 on one end, permitting the entire mating portion 34 to be inserted. The sun gear tray 32 is turned such that the mating portion 34 slidably engages the slot 28 preventing the sun gear tray 32 from moving axially along a line generally parallel to line A. A second mating portion 36, having a different configuration, can be inserted into the aperture 30 and snapped into place or held in place by an interference fit, generally preventing the sun gear tray 32 from moving in any direction relative to the base member 26. Those of skill in the art will appreciate that other attachment devices and/or methods can be used in place of the attachment configurations described above.

In some embodiments, the base member 26 is configured to engage a back cover 102 (FIG. 1) of the hinge assembly 16. In some embodiments, the base member 26 may be attached to the medial or the lateral hinge plate of the hinge assembly 16. In yet other embodiments, the base member 26 may itself comprise the medial or the lateral hinge plate. In some embodiments, the base member 26 is integrally formed with the sun gear 40 and includes ratcheted edges that are configured to engage the ring gear 52. In such case, the sun gear tray 32 is no longer used. In yet other embodiment, the base member 26 may include at least one slot 28 and/or aperture 30 for receiving a portion or portions of the sun gear tray 32. The base member 26 may further include additional apertures and/or slots for fastening the base member 26 to the hinge assembly 16.

The pad adjustment system 24 also includes the sun gear 40 operatively connected to the hinge assembly 16. In some embodiments, the sun gear tray 32 is integrally formed with the sun gear 40. As shown in FIG. 2, the sun gear 40 is located generally in the central area of the sun gear tray 32 and has a plurality of gear teeth 104 formed on its radially outer surface 106. In yet other embodiments, the sun gear 40 can be fastened to the sun gear tray 32 and fixedly held in place with fasteners. In yet other embodiments, the pad adjustment system 24 includes a sun gear 40 fixedly attached to the hinge assembly without a sun gear tray 32. Those skilled in the art will appreciate that a sun gear 40 can be operatively connected to a portion of the hinge assembly 16 in various other manners.

With reference to FIG. 2, three planetary gears 42 surround the sun gear 40. As shown, each of the planetary gears 42 include a plurality of gear teeth 108 formed on their radially outer surfaces 110 configured to contact the corresponding gear teeth 104 of the sun gear 40. The planetary gears 42 are free to rotate about their own axes, as well as revolve about the sun gear 40. As the planetary gears revolve around the sun gear, they drive a telescope plate or other driven member laterally to unload the knee, as is explained more fully below.

While a single sun gear and three planetary gears are shown, other numbers and variations of sun and planetary gears are also possible. For example, in some embodiments, the pad adjustment system 24 includes one sun gear and four planetary gears. Additionally, while the planetary gears 42 of the present embodiment are smaller in diameter than the sun gear 40, in other embodiments they can be the same size, or larger.

With continued reference to FIG. 2, the bottom surface of each planetary gear 42 remains in sliding contact with the sun gear tray 32 during rotation and revolution about the sun gear 40. Lubricant may be used to promote ease of gear movement. In other embodiments, at least one of the planetary gears 42 may be positioned at some distance axially along a line parallel to line A from the sun gear tray 32, such that a gap is formed between the planetary gear 42 and the sun gear tray 32, thereby reducing the need for lubricant.

As shown in FIG. 2, each planetary gear 42 includes a set of threaded grooves on a radially inner surface. The threaded grooves are configured to receive threaded fasteners 44. Alternatively, threaded inserts 48 may be provided. The threaded inserts 48 are inserted into apertures formed by the radially inner surfaces of the planetary gears 42 and held in place by, for example, an interference fit. As shown in FIG. 2, the threaded insert 48 includes an elongated slit 50 configured to fit over a corresponding flange or tab (not shown) within the planetary gear 42 to help hold the insert 48 in place. In other embodiments, a press-fit, injection molded or thermal welded fastener may be used. Each of the threaded inserts 48 may include a set of threaded grooves on their radially inner surfaces configured to receive a threaded fastener 44. Those of skill in the art will appreciate that other attachment devices and/or methods can be used in place of the attachment configurations described above.

FIGS. 2 and 3 show the pad adjustment system 24 including a ring gear 52 having a generally annular-shape and being configured to contact and drive the gear teeth 108 of at least one of the planetary gears 42. For example, the ring gear 52 includes a radially inner surface with a set of gear teeth 112 configured to contact the gear teeth 108 of the planetary gears 42. As the ring gear 52 is turned, the gear teeth 112 of the ring gear 52 drive the teeth of the planetary gears 42, causing the planetary gears to rotate and revolve about the sun gear 40.

The ring gear 52 also includes grip portions 54 located circumferentially around its radially outer surface 116. The grip portions 54 provide added frictional support for turning the ring gear 52 by hand. For example, the grip portions 54 include a series of generally flat, oval-shaped sections 54*a* spaced circumferentially around the ring gear 52. By providing the grip portions 54, the ring gear 52 is more easily turned by hand. Those of skill in the art will appreciate that other configurations and/or geometries of the ring gear can also be used to achieve substantially the same result. For example, the ring gear 52 may have a generally annular inner surface with teeth as described above, and a generally hexagonal (or other shaped) outer surface configured to be gripped by hand. Alternatively, different numbers of grip portions 54 may be used. In some embodiments, cup-shaped portions, as opposed to flat portions, may be used. In yet other embodiments, portions of the radially outer surface of the ring gear 52 may include friction pads or material which can aid in gripping and turning the ring gear 52 in one direction and/or another.

The pad adjustment system 24 also includes a cover plate 56 attached to the ring gear 52. As shown in FIG. 2, the cover plate 56 includes at least one aperture 58. The cover plate 56 is sized to fit over one side of the ring gear 52 so as to generally cover the planetary gears 42 and help keep them in contact with the sun gear 40. The apertures 58 are large enough in diameter to allow the threaded fasteners 44 to move axially in directions generally parallel to line A (i.e. laterally towards and away from the knee joint). The cover plate 56 also additionally includes an aperture and/or slot 120 for placement of a cover stop 60. Other configurations of a cover plate are also possible. For example, but without limitation, the cover plate may be transparent or include a series of ribs or bars which partially cover the gears underneath. In yet other embodiments, the cover plate is formed integrally with the ring gear 52.

The cover plate 56 is prevented from moving axially along line A, away from the base member 26, via the cover stop 60. The cover stop 60 may have a variety of configurations, including but not limited to the cup-like configuration shown in FIGS. 2 and 3. As shown, the cover stop 60 fits over the cover plate 56, with a lower portion extending towards the sun gear 40. In at least one embodiment, the cover stop 60 is secured in place in a hollowed-out portion of the sun gear 40 through an interference fit or with a fastener or fasteners. In at least one embodiment, the cover stop 60 remains stationary, while still allowing the ring gear 52 and cover plate 56 to rotate. Lubrication may be used between the cover stop 60 and cover plate 56 to promote ease of movement. In yet other embodiments, a portion or portions of the cover stop 60 rotate with the ring gear 52 and cover plate 56. In yet other embodiments, a cover stop is not used. For example, in some embodiments the ring gear 52 and planetary gears 42 are inhibited from slipping away from the base member 26 via their engagement with each other and the sun gear 40.

The pad adjustment system 24 also includes a telescoping plate 62. As shown in FIGS. 2 and 3, the telescoping plate 62 includes at least one apertures and/or slots 64. In some embodiments, the apertures and/or slots 64 hold the heads 45 of the threaded fasteners 44 in place, preventing the threaded fasteners 44 from rotating about their own axes as they translate axially along lines generally parallel to line A (i.e. moving towards or away from the knee joint). Those of skill in the art will appreciate that other attachment devices and/or methods may be used in place of the attachment configurations described above. The telescoping plate 62 further includes a condyle pad (not shown) on one or both of its sides. As the telescoping plate 62 is moved axially away from the base member 26 (and consequently, towards the knee joint), the condyle pad presses against a joint and provides added support to the joint.

Figure 5:
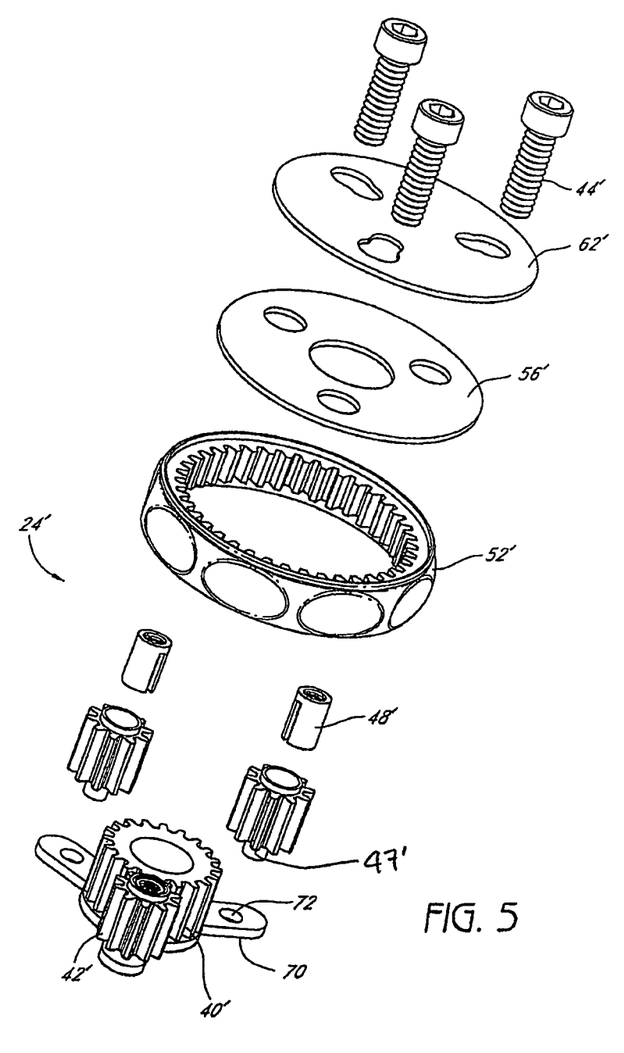
FIG. 5 is a top, front, and left side exploded view of another embodiment of a pad adjustment system.

FIG. 5 illustrates another embodiment of a pad adjustment system. Unless otherwise described below, the component numbers in FIG. 5 correspond to those of FIGS. 2-4, except that a prime indicator (') has been added to each component number. Except as noted, the descriptions of the various methods of use and the structures of the embodiment of FIGS. 2-4 apply to the following embodiment as well.

With reference to FIG. 5, a pad adjustment system 24' includes a rotary member 70. The rotary member 70 includes at least one aperture 72 for receiving a portion of a planetary gear member 42'. The rotary member 70 further includes an aperture (not shown) through which a portion of a sun gear 40' can be placed to join the sun gear 40' to the rotary member 70. The sun gear 40' may be attached to or made integral with a fixed portion of the brace assembly 10, such that it remains fixed while the rotary member 70 and planetary gears 42' rotate about the sun gear 40'.

With continued reference to FIG. 5, the planetary gears 42' include a lower prong or other portion configured to rest or sit within the apertures 72. As shown, the planetary gears 42' include protruding cylindrical portions 47', the cylindrical portions 47' having diameters smaller than that of the apertures 72. Lubrication is placed along the apertures 72 and/or on the protruding cylindrical portions 47' to promote ease of rotation of the cylindrical portions 47' of the planetary gears 42' within the apertures 72. Those of skill in the art will appreciate that other attachment devices and/or methods can be used in place of the attachment configurations described above. The depicted pad adjustment system 24' further includes threaded fastener inserts 48', a ring gear 52', a cover plate 56', threaded fasteners 44', and a telescoping plate 62' similar to the previous embodiment described above.

The pad adjustment systems described above are compact, durable, and can easily be taken apart, replaced, and/or maintained. Each component of the pad adjustment system described above may be made from moldable plastic or other suitable material. For example, in at least one embodiment the gears are injection molded from PET, PVC, PP, or other plastic, while the telescoping plate and fasteners may be made from lightweight metal.

The pad adjustment systems described above are also easy to use and operate. For example, and with reference to FIGS. 1-4, a telescoping plate 62 and condyle pad may be moved both towards and away from a knee joint by simply turning the ring gear 52 in one direction or another by hand. No screwdriver or other tool is needed to operate and adjust the pad's position.

In one exemplary implementation, as the ring gear 52 and cover plate 56 are turned, the gear teeth 112 on the ring gear's radially inner surface 114 engage the planetary gears 42. At the same time, the planetary gears 42 engage a fixed sun gear 40. As the ring gear 52 is turned, the planetary gears 42 rotate about their own axes, as well as revolve about the sun gear 40. The threaded grooves 122 on the planetary gears' radially inner surfaces (or the radially inner surfaces of their threaded inserts) rotate as well.

Because the heads of the threaded fasteners 44 are fixedly restrained by the telescoping plate 62, the threaded fasteners 44 are forced to move axially along lines generally parallel to line A as the planetary gears rotate. Thus, as the ring gear 52, cover plate 56, and fasteners 44 all revolve about the sun gear 40, the fasteners simultaneously move along lines generally parallel to line A and normal to the plane of rotation of the ring gear 52, forcing the telescoping plate 62 to move towards or away from the knee joint (see FIG. 1).

By incorporating an independent pad adjustment system attached to a hinge assembly of a knee brace, material wear and tear may be reduced. For example, once the knee brace is fastened, the ring gear 52 can be turned by hand until the telescoping plate 62 and the condyle pad reach the knee joint and apply a desired level of pressure on the joint. The pad adjustment system then remains stationary while the arms 12 and 14 pivot about the hinge assembly 16.

Additionally, by incorporating a ring gear 52 with grip features 54, the pad adjustment system may conveniently be operated by a single hand. Thus, if the comfort level or adjustment of the telescoping plate and pad require adjustment, the knee brace user can quickly and easily make an adjustment by turning the ring gear 52 in one direction or another.

Figure 6A:
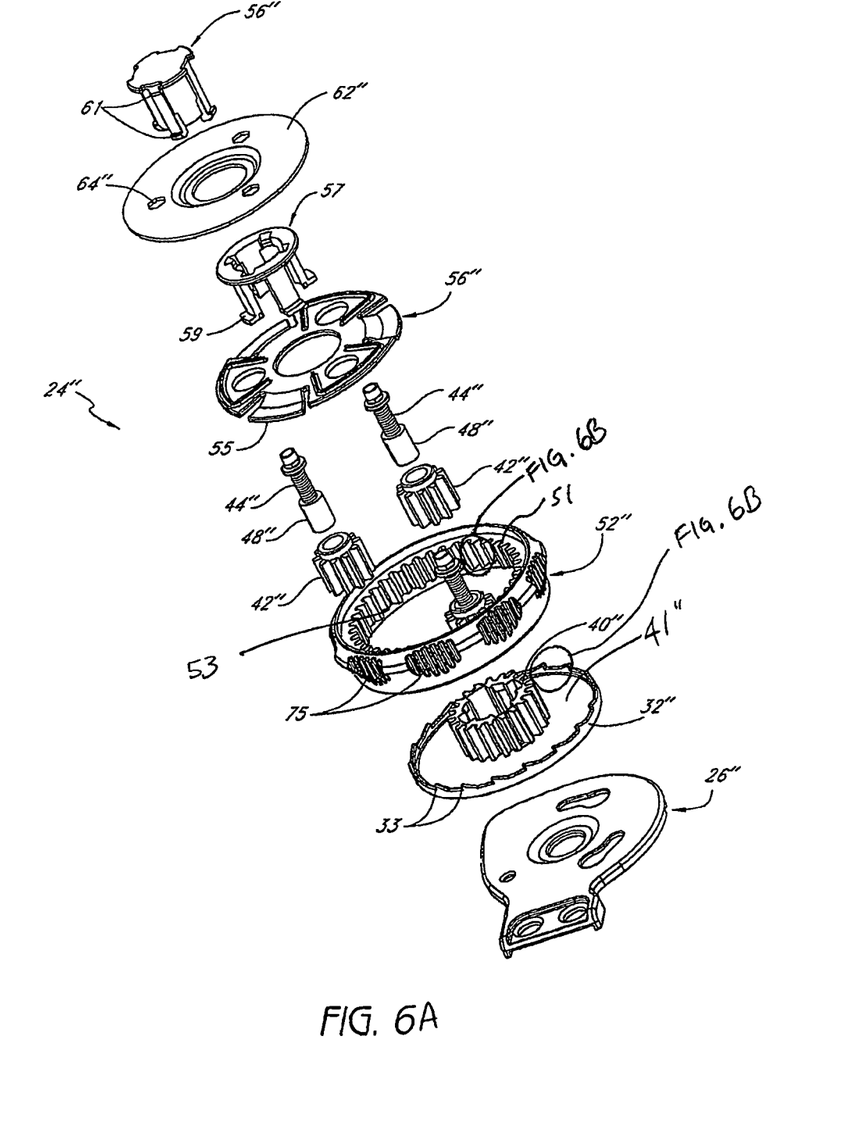
FIG. 6A is a top, front and right side exploded view of a modified embodiment of a pad adjustment system.

FIG. 6A illustrates another embodiment of a pad adjustment system 24". Unless otherwise described below, the component numbers in FIG. 6A correspond to those of FIGS. 2-5, except that a prime indicator (") has been added to each component number. Except as noted, the descriptions of the various methods of use and the structures of the embodiment of FIGS. 2-5 apply to the following embodiment as well.

The pad adjustment system 24" may include a condyle pad (not shown) which pushes against the knee joint line to unload an opposing meniscal compartment. The condyle pad may be made from foam, gel, or any other material which provides comfort to the user. With reference to FIG. 6A, the condyle pad is attached to the telescoping plate 62" of the assembly 24".

As shown in FIG. 6A, the pad adjustment system 24" further includes a cover stop 56". The cover stop 56" prevents the telescoping plate 62" from becoming disengaged from the assembly 24" as the telescoping plate 62" is moved to its farthest position (i.e. when it is laterally farthest away from the rest of the assembly 24"). As shown, the cover stop 56" also includes locking features 61 which help to lock the cover stop 60" in place in the assembly 24". As depicted, the telescoping plate 62" also includes keyed apertures 64" to inhibit the threaded fasteners 44" from rotating about their center axes and to hold the threaded fasteners 44" in place. In some embodiments the fasteners 44" are held in place by riveting, an adhesive, or a press-fit. FIG. 6A shows the pad adjustment assembly 24" having a gear cover retainer 57 and gear cover plate 56". The gear cover retainer 57 secures the gear cover plate 56" to the assembly 24" while permitting the gear cover plate 56" to rotate about the gear cover plate's central axis. As shown, the gear cover retainer 57 includes locking features 59 which lock into the bottom side of the sun gear 40" or the sun gear tray 32".

The gear cover plate 56" covers the planetary gears 42" to prevent contamination and retain the planetary gears 42" within the assembly, while still allowing the planetary gears 42" to rotate about their own axes. The gear cover plate 56" also include features 55 which can act as leaf springs that push the ring gear 52" down on the sun gear tray 32". This leaf spring action helps to keep the ring gear 52" in contact with the sun gear tray 32" and prevent the ring gear 52" from rotating in an unintended direction. The ring gear 52" may be made from several material including but not limited to plastics.

With continued reference to FIG. 6A, the sun gear 40" is secured to or may be integrally formed with the sun gear tray 32" and remains fixed in position. The sun gear tray 32" includes a sun gear tray plate 41" that receives and houses the sun gear 40'. The sun gear tray 32" is secured to a base member 26, which can be part of or integral to one of the hinge plates of the hinge assembly 16. Engagement of the sun gear tray and the ring gear member are now explained.

With continued reference to FIG. 6A, the threaded fasteners 44" telescopes towards and away from the knee joint and is threaded inside the planetary gears 42" in a threaded insert 48". The planetary gears 42" can each be geared to rotate at the same rate to ensure that each telescoping fastener 44" threads and unthreads evenly and, in turn, moves the telescoping plate 62" evenly.

Figure 6B:
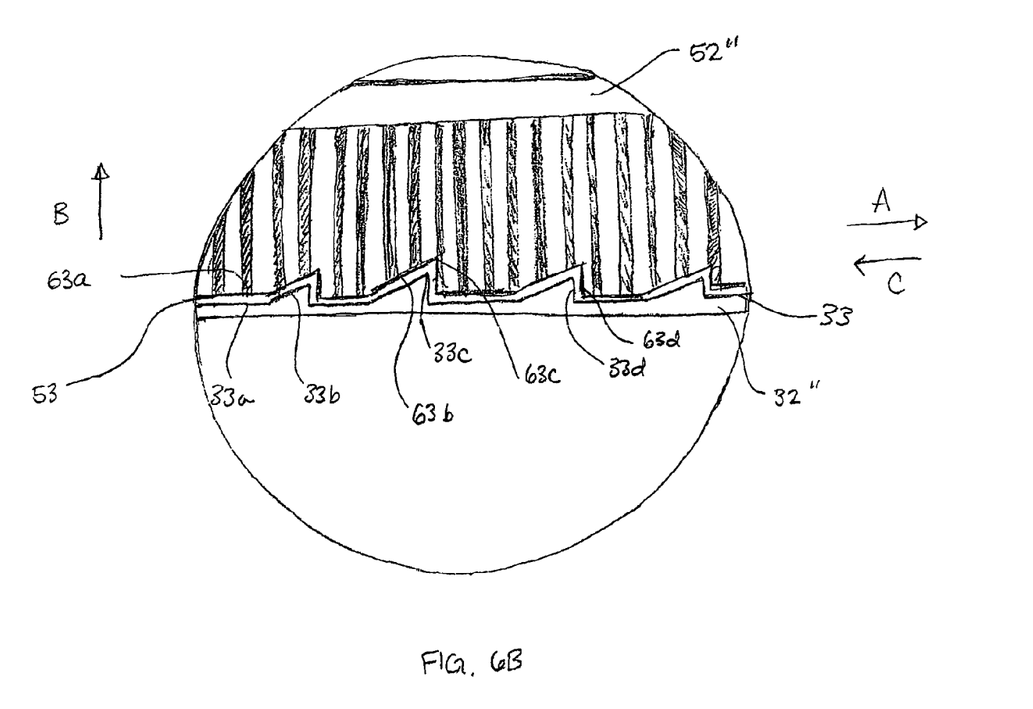
FIG. 6B shows an enlarged view of a portion of a ring gear and a portion of a sun gear tray being engaged to one another according to an illustrative embodiment of the invention.

In use, turning the ring gear 52" causes the planetary gears 42" to rotate around the sun gear 40". As shown in FIGS. 6A and 6B, the ring gear 52" includes an internal edge 53 spaced around the interior of the ring gear 52" such that it engages the sun gear tray's ratcheted edge 33. The internal edge 53 engages the ratcheted edge 33 of the sun gear tray 32" to allow ease of rotation of the ring gear 52" in one direction and prohibit the rotation of the ring gear 52" in the opposite direction. In the illustrated arrangement, the ratcheted edge 33 comprises a sawtooth-like configuration but other shapes and other ratchet-like mechanisms can be used in other embodiments.

As shown in FIG. 6B, the ratcheted edge 33 includes a series of engagement ports that receive and engage the ratcheted connection protrusions on the ring gear member. Each of the engagement ports includes a flat portion 33a and a sloped portion 33b, which are configured to engage a complementary flat portion 63a and a sloped portion 63b of the internal edge 53 of the ring gear 52." FIG. 6B shows an enlarged view of a portion of the ring gear 52" and a portion of the sun gear tray 32" being engaged to one another and when the ring gear 52" is stationary with respect to the sun gear tray 32". Starting from the configuration as depicted in FIG. 6B, when a user turns the ring gear 52" in a direction noted by Arrow A in FIG. 6B, the flat portion 63a of the ring gear 52" contacts and presses against the sloped portion 33b of the sun gear tray 32", during which the flat portion 63a is forced to move along the sloped portion 33b in direction of Arrow A. In some embodiments, such interaction produces clicking sounds, as each of the tooth protrusions 33c slide along the ring gear 52" until they slip into corners 63c.

In the illustrated arrangement, the leaf springs 55 bias the ring gear 52" towards the sun gear tray 32". In this manner, in a first condition, the teeth on the underside of the ring gear 52" are biased toward the ratcheted edge 33 of the tray 32". In this condition, it is difficult to rotate the ring gear 52" in a direction opposite to the ratcheted edge 33. When the protrusions are engaged, with protrusion 33c slotted against corners 63c, ledges 33d abut walls 63d, thereby preventing the sun gear tray 32" from revolving backward along Arrow C. To allow rotation in the opposite direction, the ring gear 52" is lifted towards the condyle pad 74 (i.e. away from the tray 32" and ratcheted edge 33). In this manner, the gear teeth 51 are disengaged from the ratcheted edge 33 and the ring gear 52" can be rotated in a direction opposite to the ratcheted edge 33.

Figure 7:
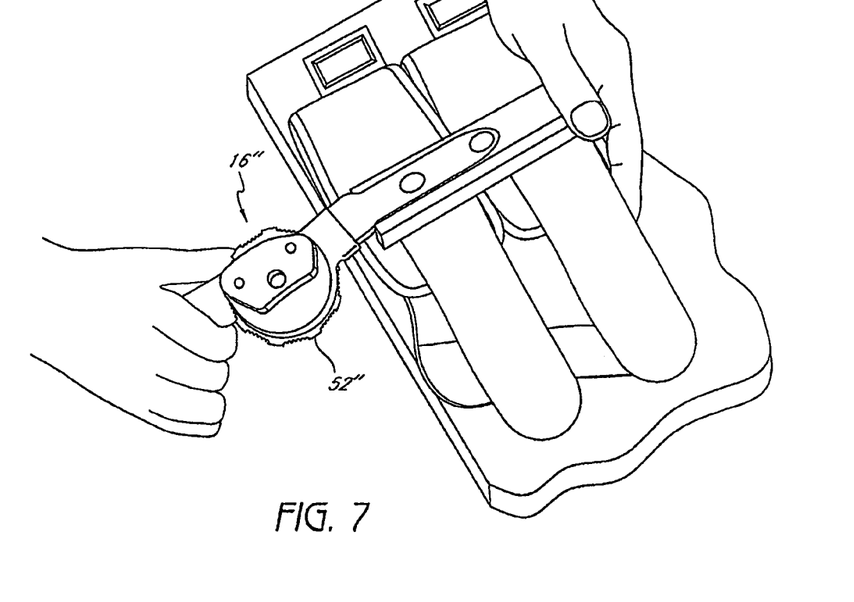
FIG. 7 illustrates a method for adjusting the knee brace of FIG. 1.

With reference now to FIG. 7, the knee braces described above can be adjusted prior to use to create a better fit for the user, and to ensure that the condyle pad makes full contact with the knee joint during use. For example, the brace 10" is placed on a sturdy table such that the hinge assembly 16" extends off an end of the table, as illustrated in FIG. 7. With the hinge assembly 16" extending off an edge of the table, one can slowly apply pressure to the hinge assembly 16", causing at least one of the proximal and distal arms 12", 14" to bend into a desired shape.

Once the proximal and/or distal arms 12", 14" are bent, the brace 10" is placed on a user's leg. Straps or cuffs on the brace 10" are secured, and one can visually inspect whether the pad on the pad adjustment system 24" makes full contact with the medial or lateral portion of the user's knee joint.

The telescoping plate 62" is adjusted by rotating the ring gear 52" as described above. For example, in some embodiments the ring gear 52" is rotated counterclockwise to move the telescoping plate 62" towards the knee joint. The ring gear 52" may be rotated until a desired level of adjustment is achieved. In some embodiments, the amount of force required to cause displacement of the telescoping plate 62" increases as the ring gear 52" is turned, making it more difficult to further adjust the telescoping plate 62". When this occurs, the proximal and distal arms 12", 14" can again be adjusted such that the arms 12" and 14" are bent closer to the knee near the pad adjustment system 24".

In some embodiments, the ring gear 52" is configured to rotate more easily in one direction than another. For example, the sun gear tray 32" can include a ratcheted edge 33, as illustrated in FIG. 6. The ratcheted edge 33 can inhibit rotation of the ring gear 52" in one direction, while permit rotation of the ring gear 52" in the opposite direction. In some embodiments, the ring gear 52" is permitted to rotate more easily in the direction which causes the telescoping plate 62" to move away from the sun gear tray 32" and towards the knee joint.

Figure 8:
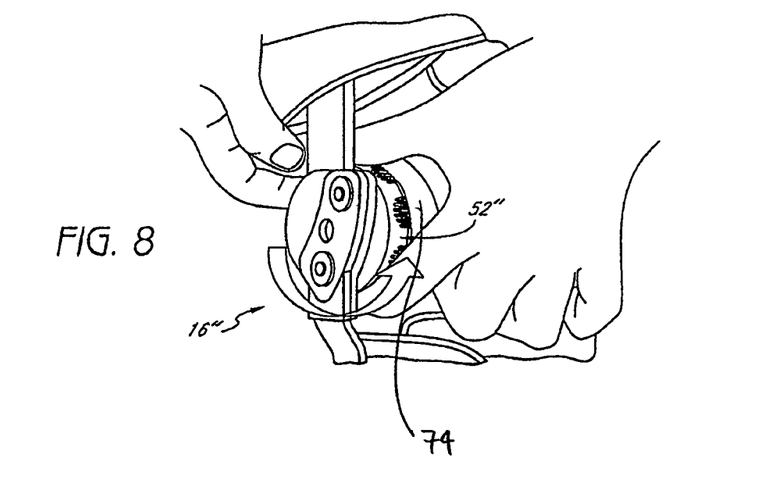
FIG. 8 illustrates a method for adjusting the pad adjustment system of FIG. 2 and FIG. 6A.

In some embodiments, to decrease the load applied by the telescoping plate 62" and move the telescoping plate 62" back towards the sun gear tray 32", the ring gear 52" is squeezed or compressed by a user's hand, as illustrated in FIG. 8. At the same time, the ring gear 52" is pushed by the user's hand towards the condyle pad 74. More specifically, as shown in FIG. 6B, the internal edge 53 of the ring gear 52" disengages from the sun gear tray 32" when the user pulls the ring gear 52" in a direction as indicated by Arrow B. As the ring gear 52" is compressed and pulled away from the sun gear tray 32", the ring gear's gearing disengages from the ratcheted edge 33, and can thus be turned in a direction which causes the telescoping plate 62" to move back towards the sun gear tray 32". In some embodiments, an additional intermediary piece is incorporated on the ring gear 52" and/or sun gear tray 32" to allow a user to pull the ring gear 52" into a locked outward position while the rotation of the ring gear 52" is adjusted. In order to relock the ring gear 52", the ring gear 52" could then be pushed back into the sun gear tray 32" to re-engage the locking feature.

Although these inventions have been disclosed in the context of certain embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combinations or sub-combinations of the specific features and aspects of the embodiments can be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above. References disclosed herein are incorporated by reference.

What is claimed is:

1. A knee brace assembly comprising:
a hinge assembly;
a proximal arm pivotably engaging the hinge assembly;
a distal arm pivotably engaging the hinge assembly; and
a pad adjustment system comprising:
a first gear member operatively connected to a portion of the hinge assembly;
a second gear member engaged with the first gear member and configured to rotate within the pad adjustment system;
a third gear member engaged with the second gear member and being actuatable by a user; and
a driven member operatively connected to the second gear member and configured to extend away from the hinge assembly upon actuation of the third gear member.

2. The knee brace assembly of claim 1, wherein:
the first gear member is a sun gear operatively connected to a portion of the hinge assembly;
the second gear member is a planetary gear engaged with the sun gear, the planetary gear comprising a set of gear teeth and threaded grooves;
the third gear member is a ring gear engaged with the planetary gear;
the driven member is a threaded fastener partially received within the threaded grooves of the planetary gear; and
further comprising a telescoping plate connected to the fastener.

3. The knee brace assembly of claim 2, wherein the pad adjustment system comprises at least one additional planetary gear configured to engage with and revolve around the sun gear.

4. The knee brace assembly of claim 2, further comprising a base member configured to connect to the hinge assembly, and a sun gear tray integrally formed with the sun gear, the sun gear tray configured to connect to the base member.

5. The knee brace assembly of claim 4, further comprising a ratchet mechanism between the sun gear tray and the ring gear.

6. The knee brace assembly of claim 2, wherein the planetary gear is configured to both revolve about the sun gear and rotate about the planetary gear's own axis.

7. The knee brace assembly of claim 2, wherein the threaded grooves are located on a fastener insert positioned in the planetary gear.

8. The knee brace assembly of claim 2, wherein the ring gear comprises a set of gear teeth on an inner annular surface configured to contact the planetary gear.

9. The knee brace assembly of claim 2, wherein the ring gear comprises at least one gripping surface along a radially outer surface.

10. The knee brace assembly of claim 9, wherein the at least one gripping surface comprises a cup-shaped section of material on the ring gear.

11. The knee brace assembly of claim 1, further comprising a locking member engaged with the third gear member by a locking ledge.

12. The knee brace assembly of claim 11, wherein the locking ledge comprises a plurality of ratcheting protrusions configured to engage grooves on the third gear member.

13. The knee brace assembly of claim 12, wherein the ratcheting protrusions resist rotation between the third gear member and first gear member in at least one direction.

14. The knee brace assembly of claim 2, wherein the threaded fastener is configured to attach to the telescoping plate in a manner which prevents rotation of the threaded fastener.

15. The knee brace assembly of claim 1, wherein the third gear member is rotatably actuatable by a patient or physician.

16. The knee brace assembly of claim 1, further comprising a pad coupled to the driven member.

17. The knee brace assembly of claim 1, further comprising a cover plate for a gear member.

18. The knee brace assembly of claim 1, further comprising a cover stop configured to prevent the gear member from translating axially.

19. A knee brace assembly configured to off-load a patient's knee, comprising:
   a gear system coupled to an inner side of a hinge assembly of the knee brace, the gear system comprising:
      a first gear;
      a plurality of second gears engaged with the first gear;
      a third gear in rotating engagement with the second gears;
      a telescoping plate engaged with the second gear by a coupling; and
   wherein rotation of the third gear causes the telescoping plate to be displaced along the coupling.

20. A method for adjusting the amount of pressure applied to a knee joint comprising:
   securing a gear system to an inner side of a hinge assembly of a knee brace;
   turning, by hand, a knob of the gear system that engages with and simultaneously causes a plurality of revolving gear members to drive a telescoping plate towards or away from the knee joint; and
   adjusting the position of the telescoping plate until a desired level of pressure against the knee joint is achieved.

* * * * *